(12) United States Patent
Callahan et al.

(10) Patent No.: US 6,622,855 B1
(45) Date of Patent: Sep. 23, 2003

(54) INTRAOCULAR LENS CASE

(75) Inventors: Wayne B. Callahan, Roanoke, VA (US); Jeffery S. Callahan, Blountville, TN (US); Joseph D. Callahan, Abingdon, VA (US)

(73) Assignee: ThinOptX, Inc., Abingdon, VA (US)

( * ) Notice: Subject to any disclaimer, the term of this patent is extended or adjusted under 35 U.S.C. 154(b) by 40 days.

(21) Appl. No.: 10/066,296

(22) Filed: Jan. 30, 2002

Related U.S. Application Data
(60) Provisional application No. 60/265,397, filed on Jan. 30, 2001.

(51) Int. Cl.[7] .............................................. B65D 81/24
(52) U.S. Cl. ...................................... 206/5.1; 623/6.11
(58) Field of Search ................. 206/5.1, 438; 623/6.11; 128/898; 356/246; 606/107

(56) References Cited

U.S. PATENT DOCUMENTS

| | | |
|---|---|---|
| 4,087,866 A | 5/1978 | Choyce et al. |
| 4,451,938 A | 6/1984 | Kelman |
| 4,508,216 A | 4/1985 | Kelman |
| 4,684,014 A | 8/1987 | Davenport |
| 4,736,836 A | 4/1988 | Alongi et al. |
| 5,199,559 A | 4/1993 | Dark |
| 5,281,227 A | 1/1994 | Sussman |
| D360,068 S | 7/1995 | Hambleton et al. |
| D382,399 S | 8/1997 | Hambleton et al. |
| 6,083,261 A | 7/2000 | Callahan et al. |
| 6,096,077 A | 8/2000 | Callahan et al. |

*Primary Examiner*—David T. Fidei
(74) *Attorney, Agent, or Firm*—Waddey & Patterson, P.C.; Douglas W. Schelling

(57) ABSTRACT

A lens case for a refractive or non-refractive intraocular lens having a support disk for the optic. The case is designed to provide protection and support during washing, sterilization, shipping, and storage. This case has a removable disk that provides a work surface for surgery. Additional features assist in the washing and sterilization of the lens.

17 Claims, 5 Drawing Sheets

Figures

INTRAOCULAR LENS CASE

This application claims priority under 35 U.S.C. §119(e) to U.S. provisional application No. 60/265,397, filed Jan. 30, 2001, the contents of which is incorporated herein in its entirety.

FIELD OF THE INVENTION

The present invention relates to the field of refractive intraocular lens or traditional intraocular lens (IOL) cases. More particularly, the present invention relates to cases and packages for holding, carrying, and storing anterior, posterior, or refractive IOLs.

BACKGROUND OF THE INVENTION

After World War II Harold Ridley, an English ophthalmologist started implanting lens in the human eye after cataract surgery. By the late 1970's D. Peter Choyce had developed several models of anterior chamber lenses. One such model is described under U.S. Pat. No. 4,087,866. The design was solid and fit in the anterior chamber of the eye. The sizing to fit the eye was critical. The lenses were manufactured in overall lengths of 14.0 to 11.5 millimeters in 0.5-millimeter increments. The footplate thickness was approximately 250 microns. This style lens was very rigid. As such, lens cases designed to hold, carry, and store this type lens did not have to supply the protection that current thin lens designs require.

As lenses became more advanced, several styles of lenses with large sweeping haptics that rested in the anterior angle between the cornea and iris were attempted. These haptics were designed to hold the lens precisely in place. With respect to these early designs, in some cases the sweeping haptics blocked the trabecula mesh work, which caused glaucoma.

Charles Kelman disclosed in U.S. Pat. No. 4,451,938 that the round footplates of the Choyce lenses were more effective if they were attached to a flexible member. The Kelman designs had much better flexibility. Although one size was not available for all eyes, these lenses were more adaptable. The common lengths of the Kelman lenses were 14.0, 13.5, 13.0, 12.5, 12.0, 11.5, and 11.0 millimeters. The thickness of the footplates on the Kelman lens varied from 250 to 175 microns. If the lens was sized too large or too small, complications were reported. However, the complication rate with the Kelman designs was a significant improvement. In fact, the Kelman lenses have been the standard of care for anterior chamber cataract lens for almost twenty years.

The typical Kelman cataract anterior chamber lens was designed to fit into the eye after cataract extraction. With the natural lens removed, the posterior capsule collapsed allowing the iris to become flat. The typical anterior chamber lens had a positive power placed on the anterior surface. The posterior surface was flat. In other designs, part of the power was cut into the posterior surface, so the lens was bi-convex. Outward from the optic the lens haptics projected posteriorly 0.5 millimeters across some distance of approximately two and one half millimeters to allow the footplates to be flat. The footplates were 175 to 250 microns. The opening of the trabecula is approximately 200 microns. Additionally, the trabecula was blocked where the footplates were touching the tissue.

If the lens was slightly larger than the eye and pressed against the tissue, some indentation would occur, which increased the blocked area of the trabecula. Even though the Kelman lenses were a significant improvement over the state of the art—especially in terms of flexibility, they are relatively thick and fairly rigid. Therefore, such a lens would typically be thought of as not necessarily requiring a lens case that offers the protection that current lenses require.

In early development work, John Sheets, M.D., developed a glide to assist in the delicate task of inserting a lens into the eye. The glide was an extremely thin piece of sterile material, most often plastic, that was inserted into the eye and the lens placed on top of the glide. The lens was then inserted into the eye with some assurances the haptics would not catch on tissue as the lens was inserted. Once the lens was in place, the glide was removed.

Current developments include U.S. Pat. Nos. 6,083,261 and 6,096,077 to Callahan et al, which disclose thin lenses that are implanted in the eye to supplement the natural lens. Lenses disclosed in these patents are extremely thin, with respect to the state of the art. Lens development has advanced to the point where center thickness of lenses runs in the 26-micron range for myopic eyes. To secure these lenses in the eye, haptics of thin profiles have been developed. Haptic thickness is in the 150-micron range with footplates in the 50-micron range.

As lenses became thinner and were manufactured with moer precision, the need arose for better lens cases for transport, washing, sterilization, aeration, and storage that are capable of protecting the lens and providing a user-friendly platform for the surgeon implanting the lens.

There have been several prior art attempts to provide such cases. For example, lens cases designed by Hambleton et al., are disclosed in U.S. Des. Pat. No. 360,068 and U.S. Des. Pat. No. 382,399. These lens cases appear to provide some protection and limited support for the lens, but it does not appeat that enough protection is provided for the more delicate state of the art lenses.

The lens case of Stephen Dark, disclosed in U.S. Pat. No. 5,199,559, uses large holes for circulation around the lens, but does not provide support for the center portion of the lens. The clip design of one embodiment of the current patent simplifies the manufacture of the lens case, especially when compared to the cover/base arrangement disclosed in the '599 patent. Additionally, the lens cases disclosed in the '599 patent fail to have the ability to serve as an aid in washing the lens.

Lens cases like the one designed by James M. Davenport, U.S. Pat. No. 4,684,014, do not provide enough openings for degassing. Based on the design of the '014 patent, it appears that it would be difficult in complying with current limits for residual Ethylene Oxide (ETO).

Cases such as the one described in patent U.S. Pat. No. 4,736,836, Alongi et al, use complicated screw caps to hold the lens as opposed to the simple slide mechanisms on the current patent. In addition, the lens cases disclosed herein do not provide adequate support for the new thin lens designs.

The case disclosed in U.S. Pat. No. 4,508,216, to Kelman, does not appear to provide support for the lens. Furthermore, this design is not compatible with an object of the present invention to provide a lens case that also aids in washing and degassing the lens.

Finally, lens cases disclosed by Glenn Sussman, in U.S. Pat. No. 5,281,227, are for rolling lens made of softer materials. Furthermore, these cases do not provide support for the lens and are not designed for ETO sterilization.

All patents/publications discussed above, and throughout the specification are expressly incorporated herein by reference.

SUMMARY OF THE INVENTION

An embodiment of the present invention is a lens case for housing an intraocular lens or refractive lens. A lens case of this embodiment comprises a base having a top and bottom surface, and two transverse guide slots; a lens support disk with a circular, concave surface for the support of an intraocular lens or refractive lens; and a fastening device. The lens support disk is in contact with the base. The fastening device is slidably received by a guide slot that engages the base and lens support disk, and the fasenting device snugly secures the lens support disk to the base.

Accordingly, it is an object of the present invention to provide an intraocular lens case that gives proper support and protection to the lens during transport and storage.

It is another object of the present invention to provide an intraocular case that provides safe carriage and storage for a lens without damaging the lens.

It is another object of the present invention to provide a lens case that also provides a washing support for the lens, and a support for the lens during sterilization.

It is another object of the present invention to provide a lens case that provide a surgeon a working platform during surgery. Further, it is an object of the present invention to provide a lens case that offers easy access to the lens once opened.

These and other objects, features, and advantages of shall become apparent after consideration of the description and drawings set forth herein. All such objects, features, and advantages apparent to one of ordinary skill in the art are contemplated to be within the scope of the present invention even though not specifically set forth herein.

DETAILED DESCRIPTION OF THE INVENTION

The present invention provides a lens carriage and storage case for the safe containment and carriage of anterior chamber and posterior chamber IOLs and refractive lenses.

Additionally, embodiments of the lens case of the present invention are capable of protecting the lens, providing a washing support for the lens, protecting the lens during sterilization, and providing a surgeon a working platform during surgery.

The lens case of the present invention is preferably comprised of a one-piece body, with two parallel paths engaging the sliding clips that secure a circular les support disk. The lens support disk is preferably concave in shape to provide a lens a supporting surface or a resting surface, and sheaths the intraocular lens without applying pressure to the implant when attached to the base.

As stated above, an embodiment of the present invention is a lens case for housing an intraocular lens or refractive lens. A lens case of this embodiment comprises a base having a top and bottom surface, and two transverse guide slots; a lens support disk with a circular, concave surface for the support of an intraocular lens or refractive lens; and a fastening device. The lens support disk is in contact with the base. The fastening device is slidably received by a guide slot that engages the base and lens support disk, and the fastening device snugly secures the lens support disk to the base.

Figure 2:
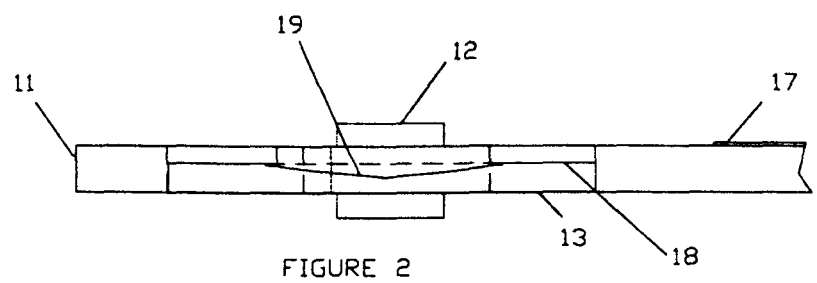
FIG. 2 is a side view of the lens support disk in the lens case with the clips in the closed position.
Figure 3:
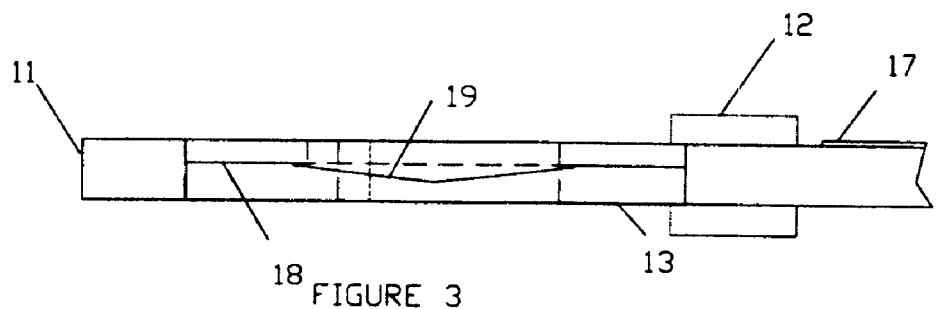
FIG. 3 is a side view of the lens support disk in the lens case with the clips in the open position.
Figure 4:
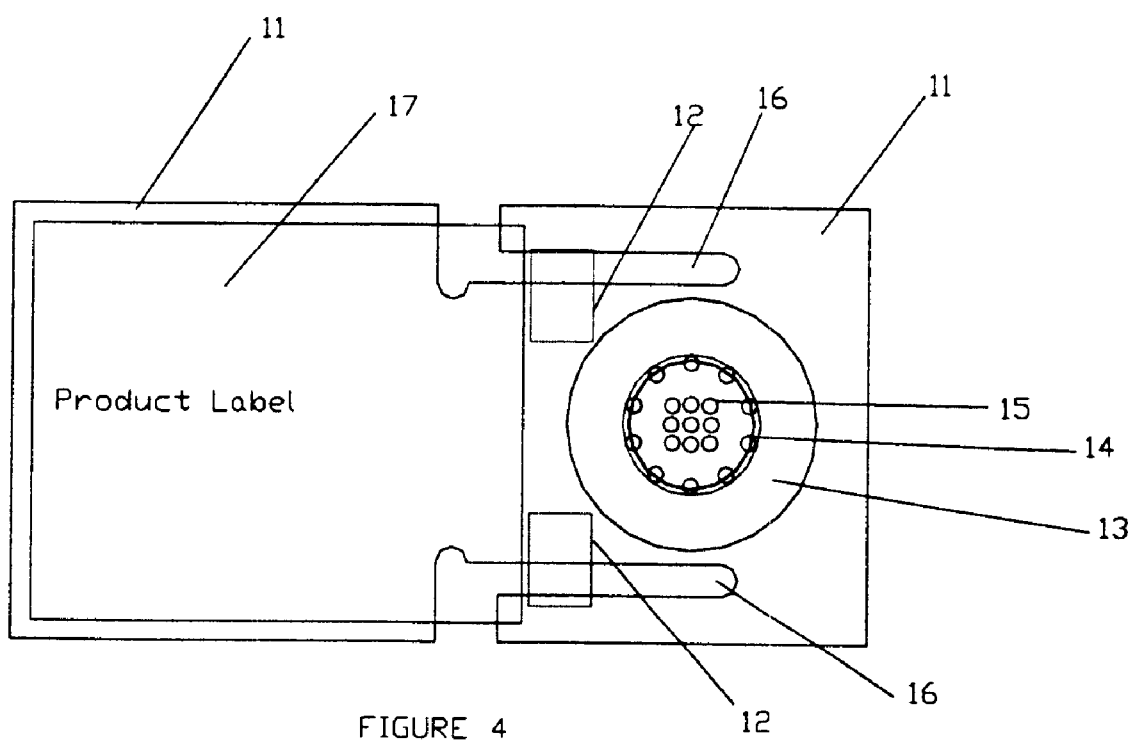
FIG. 4 is a top view of the lens case with the clips in the open position.

In another, preferred embodiment, the base further comprises a lens support disk receiving cavity that is recessed in the bottom surface of the base, and the fastening device snugly secures the lens support disk to the receiving cavity. FIGS. 2 and 3 show the support disk in communication with the receiving cavity. In the embodiments shown in FIGS. 2 and 3, the lens support disk is flush with the bottom surface of the base. Preferably, and as shown in the figures, the lens support disk is substantially circular and the disk receiving cavity is substantially circular. However, this feature is no known to be critical, and may change to suit the preferences of a user. The diameter of the receiving cavity should be larger in diameter or area than the lens support disk, so that the lens support disk can be received by the receiving cavity. As an example, the lens support disk may have a diameter of about 24–26 mm in diameter. Generally, the lens support disk must be larger than the base through hole.

The lens support disk of the present invention may have at least one through hole passing through the width of the lens support disk. Preferably, the support disk comprises at least two through holes. More preferably, through holes are present both in the center (or substantially in the center) and around the perimeter of the support disk. The through holes facilitate water flow or air flow to an intraocular lens or refractive lens. Most preferably, the base has a through hole that, in combination with the through hole(s) of the support disk, facilitate air and water flow. The base through hole is preferably in substantial alignment with at least one hole of the support disk 13. For example purposes, the support disk through hole is preferably less than 1 mm in diameter. Preferably, when one base through hole is present, the base through hole is at least 3 mm in diameter and the at least one lens support disk through hole is less than 1 mm in diameter.

As stated above, the through holes promote water flow during washing or irrigation. The preferred through holes in the perimeter of the support disk to allow better draining. This preferred arrangement allows the lens to be irrigated when still in the lens case.

The lens case of the present invention may be sterilized after a lens is secured in the case. Typically, lens and lens cases are sterilized using ETO (ethylene oxide) sterilization by, for example subjecting the case and lens to ethylene oxide for a period of sis to eight hours at 130 to 135 degrees F. The sterilization procedure for the case of the present invention may be similar to the one disclosed in U.S. Pat. No. 4,684,014. The through holes in the preferred embodiments allow better passage of the gas during sterilization and during the gas off periods.

As stated above, the lens support disk has a concave surface, or has a corresponding profile, to support or cradle the lens. Additionally, the concave surface may comprise an optic cavity that has the same design as the lens to receive an intraocular lens or a refractive lens. This cavity would include positions for the haptics and feet.

The shape of the base is not critical, and may be modified to accommodate the preferences of the user. Preferably, and for ease of manufacturing and use, the lens case base is generally rectangular and the transverse groove slots are substantially parallel to one another. As an example, the lens case of claim 10, wherein the base is about 40 mm×90 mm×4 mm.

Figure 9:
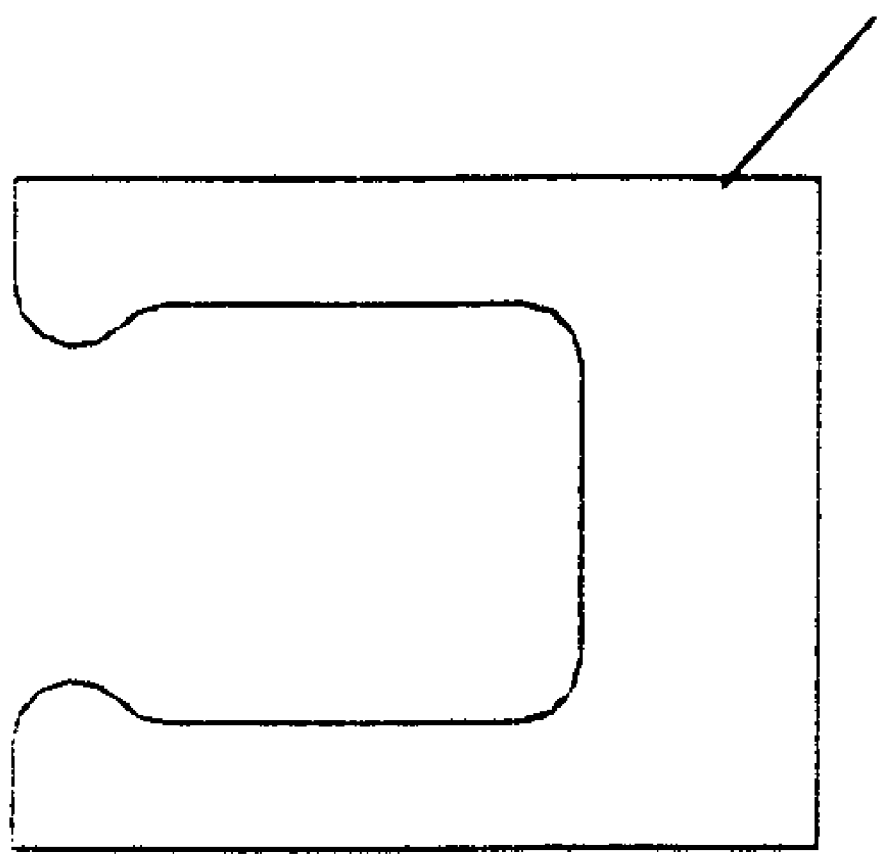
FIG. 9 is a view of a fastening device of the present invention.

The preferred fastening device is standard clips, such as those shown in FIG. 9, designated as 12.

The clips slide in grooves, slots, or channels running traverse (preferably parallel) to the edges of the lens case. The clips provide adequate force to the lens support disk to hold it firmly against the body of the lens case.

Further, it is understood that the lens case described herein and in the claims can be made by machining, molding, or any other process of manufacture. More specifically, the lens case can be injection molded in a process similar to that described in U.S. Pat. No. 5,199,559.

Figure 5:
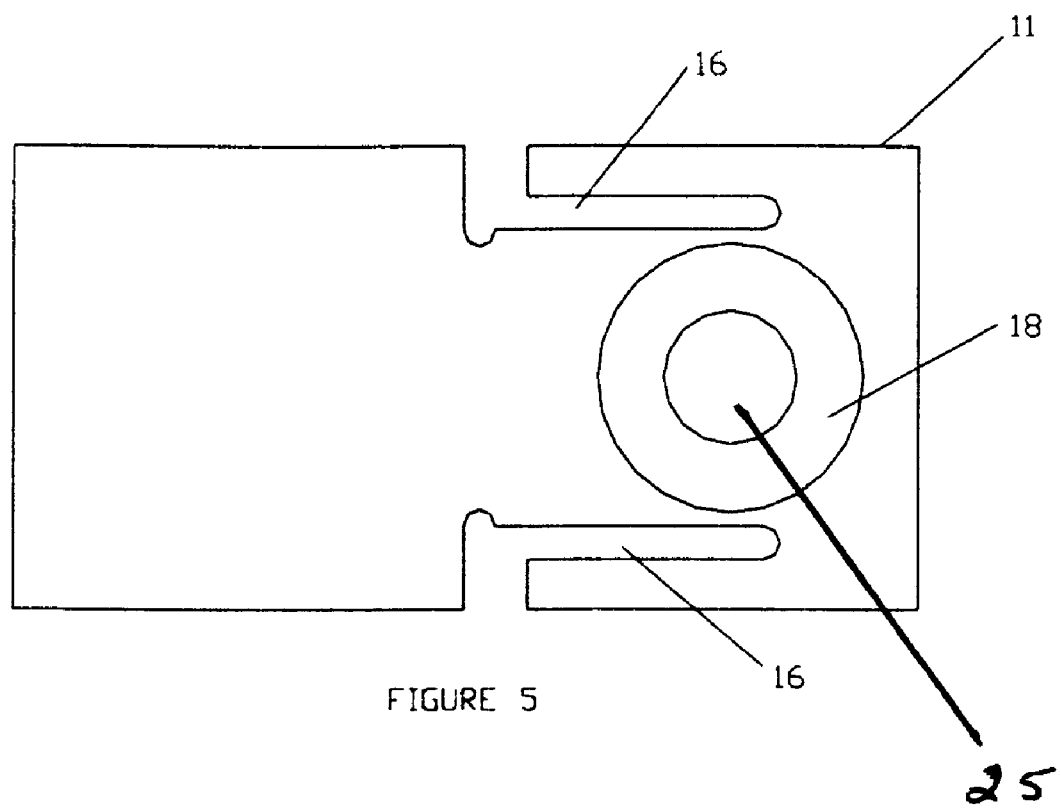
FIG. 5 is a top view of the base of the lens case.
Figure 6:
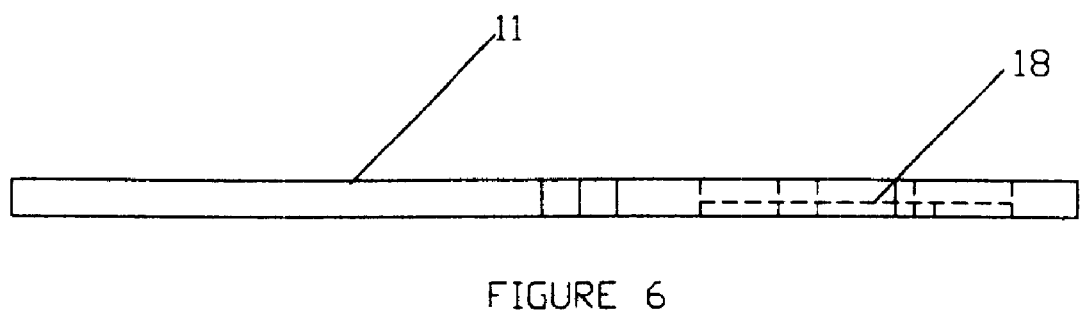
FIG. 6 is a side view of the base of the lens case.
Figure 7:
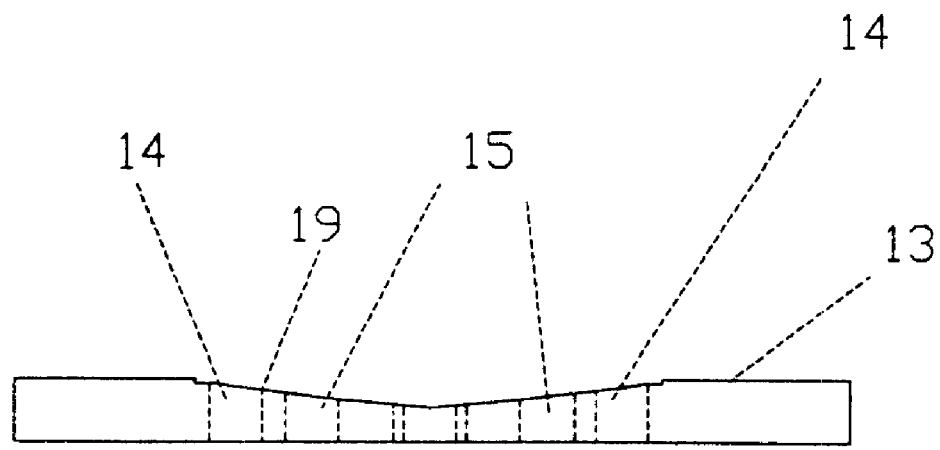
FIG. 7 is a side view of the lens support disk.
Figure 8:
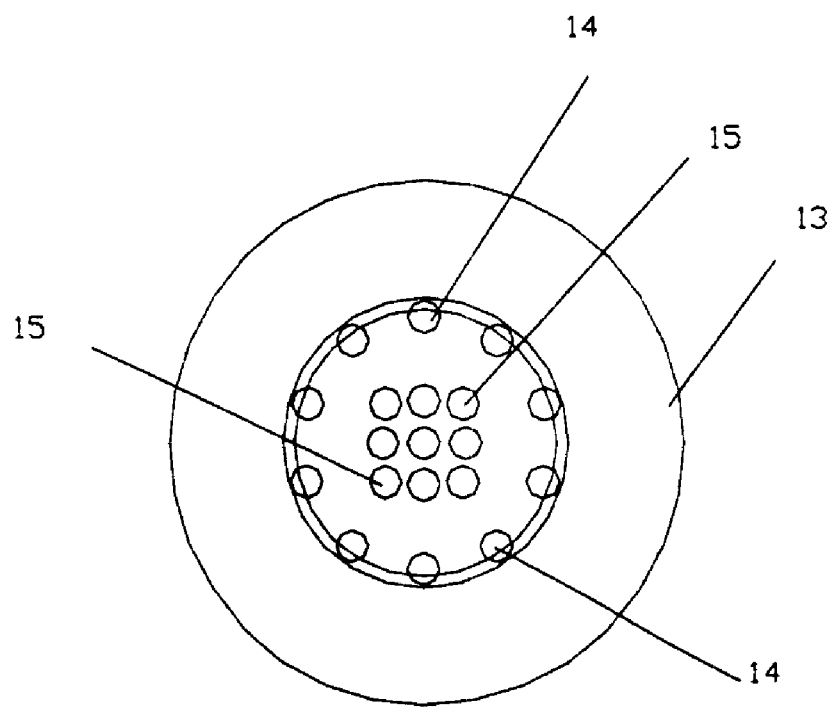
FIG. 8 is a top view of the lens support disk.

Turning to the drawings, which have consistent labeling, the figures show an example of a lens case of the present invention comprising a base 11, lens support disk 13, clips 12, intraocular lens 20 and optional product labeling 17. The clips travel along channels 16 in the base. Through holes 14, 15 are shown in the center of the support disk, and closer to the perimeter of the disk (15). The base through hole 25 is shown in FIG. 5.

Figure 1:
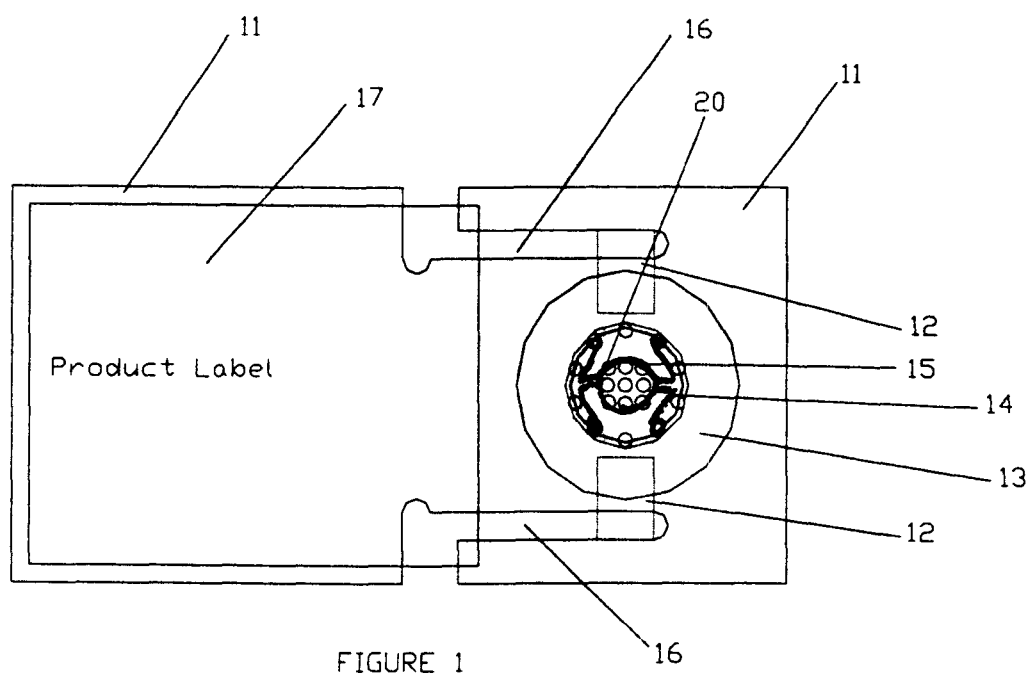
FIG. 1 is a top view of the lens case with the clips in the closed position.

The base 11, clip 12, and the lens support disk 13 can be molded or machined from any material compatible with the material of construction of the lens and method of sterilization. The completed lens case as shown in FIG. 1 can be sealed in a package (not shown) and sterilized, shipped and stored.

The base of the lens case may be a basic rectangle 11, and in a preferred embodiment, may measure approximately 40 mm×90 mm×4 mm.

A recessed disk receiving cavity 18 for the lens support disk (FIGS. 1–13) is cut in the base 11 in the embodiment shown. As shown in this embodiment, the recess for the support disk is approximately 26 mm in diameter and 1.85 mm deep to accommodate a lens support disk that is 25.4 mm in diameter and 1.8 mm thick.

A concave profile of the lens 19 may be cut into one side of the disk. The through holes 14 are preferably approximately 0.7937 mm in diameter.

Preferably, the opening in the clip 12 shown in relation to the base shown is approximately 4 mm, but depends on the thickness of the base. The clip is designed to apply enough pressure to hold the lens support disk in the lens case base.

To assemble the lens case start with the lens base FIG. 1 item 11. Insert the lens support disk 13 as shown in FIG. 2. The profile of the lens 19 should be facing the recess 18 in the lens base 11 with the flat side of the lens support disk down. Through the slots 16 insert the clips 12 and move the clips 12 to the closed position (FIG. 1 and FIG. 2). Insert the lens 20 in the lens case assembly (FIG. 1). After final washing and drying, the labeling 17 or other indicia may be applied to the lens case as shown in FIG. 1 and FIG. 2. The labeling 17 may also be designed to help prevent the clips 12 from becoming detached from the lens case assembly FIG. 1.

To remove the lens 20 from the case assembly, typically the sterile pouch will have to be opened. With the label 17 information up, the slide clips 12 are moved open position. The lens 20 along with the lens support disk 13 will drop from the bottom of the case assembly. However, the arrangement of the present invention give the surgeon options with respect to removal and irrigation. If the through holes are present, irrigation may begin before the lens is removed from the case. Additionally, the base provides a handle for ease of irrigation. Once the fasteners are removed and the support disk is removed, the lens can be further irrigated while resting on the disk. Additionally, the lens may be removed from the disk by forceps, for example without the lens being in contact with a foreign object.

As stated above, all patents and publications cited and/or references above are expressly incorporated herein by reference.

This invention thus being described, it will be obvious that the same may be varied in many ways. Such variations are not to be regarded as a departure from the spirit and scope of the present invention, and all such modifications as would be obvious to one of ordinary skill in the art are intended to be included in the scope of this invention and the following claims.

We claim:

1. A lens case for housing an intraocular lens or refractive lens, comprising:

a base having a top and bottom surface, and comprising two transverse guide slots;

a lens support disk with a circular, concave surface for the support of an intraocular lens or refractive lens, the lens support disk being in contact with the base;

a fastening device that is slidably received by a guide slot that engages the base and lens support disk, and snugly secures the lens support disk to the base.

2. The lens case of claim 1, wherein:

the base further comprises a lens support disk receiving cavity that is recessed in the bottom surface of the base, and the fastening device snugly secures the lens support disk to the receiving cavity.

3. The lens case of claim 1, wherein:

the lens support disk is substantially circular and the disk receiving cavity is substantially circular.

4. The lens case of claim 2, wherein:

the diameter of the receiving cavity is larger than the diameter of the lens support disk, so that the lens support disk can be received by the receiving cavity.

5. The lens case of claim 1, wherein the lens support disk comprises at least one through hole.

6. The lens case of claim 1, wherein the lens support disk comprises at least two through holes to facilitate water flow or air flow to an intraocular lens or refractive lens.

7. The lens case of claim 1, wherein the base has a through hole to facilitate water flow or air flow to an intraocular lens or a refractive lens that is supported by the lens support disk.

8. The lens case of claim 5, wherein the base has a through hole in substantial alignment with at least one through hole in the lens support disk to promote fluid flow or air flow.

9. The lens case of claim 5, wherein at least one through hole is in the substantial center of the of the lens support disk, and at least one through hole is on the periphery of the lens support disk.

10. The lens case of claim 1, wherein the concave surface of the lens support disk comprises an optic cavity proportioned to receive an intraocular lens or a refractive lens.

11. The lens case of claim 1, wherein the base is generally rectangular and the transverse groove slots are substantially parallel to one another.

12. The lens case of claim 11, wherein the base is about 40 mm×90 mm×4 mm.

13. The lens case of claim, 1, wherein the lens support disk is about 24–26 mm in diameter.

14. The lens case of claim 5, wherein the at least one through hole is less than 1 mm in diameter.

15. The lens case of claim 6, wherein the through holes are les than 1 mm in diameter.

16. The lens case of claim 8, wherein the base through hole is at least 3 mm in diameter and the at least one lens support disk through hole is less than 1 mm in diameter.

17. The lens case of claim 2, wherein the lens support disk is engaged by the receiving cavity in a flush relationship with respect to the bottom surface of the base.

* * * * *